United States Patent [19]

Lechtken et al.

[11] Patent Number: 4,616,016

[45] Date of Patent: Oct. 7, 1986

[54] MIXTURES WHICH PROMOTE GROWTH AND INCREASE PRODUCTION, AND FEEDS AND DRINKING LIQUIDS WHICH CONTAIN SMALL AMOUNTS OF THESE MIXTURES

[75] Inventors: Peter Lechtken, Frankenthal; Axel Nuerrenbach, Gruenstadt; Walter Kohler, Frankenthal; Peter P. Hoppe, Wachenheim; Hubert Tiefenbacher, Leinfelden-Echterdingen; Juergen Schole, Wedemark, all of Fed. Rep. of Germany

[73] Assignee: BASF Aktiengesellschaft, Ludwigshafen, Fed. Rep. of Germany

[21] Appl. No.: 597,664

[22] Filed: Apr. 6, 1984

[30] Foreign Application Priority Data

Apr. 7, 1983 [DE] Fed. Rep. of Germany ....... 3312425

[51] Int. Cl.$^4$ .................... A61K 9/40; A61K 31/50; A61K 31/47; A61K 31/535
[52] U.S. Cl. ................... 514/249; 514/312; 514/236; 424/37
[58] Field of Search ............... 514/579, 249, 312, 236

[56] References Cited

FOREIGN PATENT DOCUMENTS

P3151534.7 7/1983 Fed. Rep. of Germany ...... 514/579

OTHER PUBLICATIONS

Chemical Abstracts, vol. 77, 1972, Ref. No. 3944 m.
Chemical Abstracts,. vol. 93, 1980, Ref. No. 166 211 q.

*Primary Examiner*—Frederick E. Waddell
*Attorney, Agent, or Firm*—Keil & Weinkauf

[57] ABSTRACT

A growth-promoting additive for feeds consists of a commercial growth promoter as well as an aminoreductone of the formula

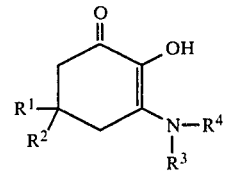

where $R^1$, $R^2$ and $R^3$ are each hydrogen, methyl or ethyl and $R^4$ is an unsubstituted or substituted $C_1$–$C_{20}$-alkyl or alkenyl radical or a radical of an aminoacid.

8 Claims, No Drawings

MIXTURES WHICH PROMOTE GROWTH AND INCREASE PRODUCTION, AND FEEDS AND DRINKING LIQUIDS WHICH CONTAIN SMALL AMOUNTS OF THESE MIXTURES

The present invention relates to mixtures, and feeds and drinking liquids which contain these, which promote growth and/or increase production, and are suitable for domestic and productive animals.

The world population is growing steadily, so that ensuring food supply, in particular the protein supply, is a great problem (cf. B. Andreae, Ernährungs-Umschau 29 (10) (1982), 324–327). Hence, it is necessary to keep the use of feed to a minimum in the production of animal protein, since this consumes, for example, grain required for human nutrition. This aim can be achieved by, for example, active ingredients which, when mixed in a small amount with the feed, promote the growth, in particular the weight gain, of domestic and productive animals, or have an advantageous effect on animal production, for example egg laying or milk output, and hence reduce the consumption of feeds.

A number of substances which promote the growth of productive animals or improve feed utilization are in use. The most important substances of this type can be found in, for example, the chapter entitled Additives in Complete Feeds in the German Feedstuffs Law. In spite of the fact that some of these compounds have a good effect, it is desirable to reduce the amount used, particularly because of their antibiotic character.

We have found, surprisingly, that if aminoreductones are combined with conventional growth promoters the latter can be used in smaller amounts, and furthermore an effective increase in weight gain or animal production can be achieved. Such aminoreductones are compounds of the general formula I

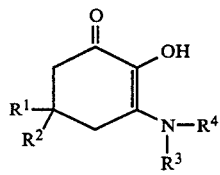

where $R^1$, $R^2$ and $R^3$ are identical or different and are each hydrogen, methyl or ethyl and $R^4$ is a straight-chain or branched $C_1$-$C_{20}$-alkyl or alkenyl group which can carry one or more hydroxyl groups, low molecular weight alkoxy groups or low molecular weight acyloxy groups, or is a radical $-(CH_2-CH_2-O)_nH$, where n is from 1 to 10, which can be etherified with a low molecular weight alkanol or esterified with a low molecular weight carboxylic acid, or is the radical, bonded at the amino group, of a natural α- or β-aminoacid or a $C_1$-$C_{10}$-alkyl ester of this, or, in the case of an α-aminoacid, is a radical in which the carboxyl group of the aminoacid and the 2-hydroxyl group of the cyclohexenone ring form a lactone, or physiologically tolerated salts thereof, which are mixed with the feed or the drinking liquids in small amounts.

Examples of suitable growth promoters (A) are compounds of the general formula II

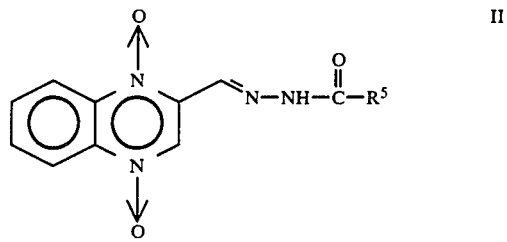

where $R^5$ is $C_1$-$C_6$-alkyl which can be substituted by halogen or cyano, or is $C_1$-$C_6$-alkoxy.

Further suitable compounds are those of the general formula III

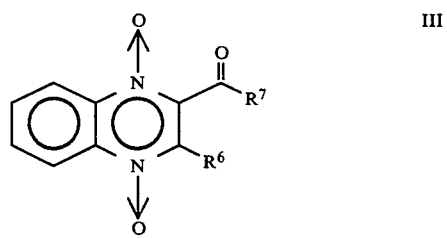

where $R^6$ is hydrogen or a low molecular weight alkyl radical and $R^7$ is a low molecular weight alkyl, alkoxy or alkylamine radical, these radicals being unsubstituted or substituted by hydroxyl or alkoxy groups.

Finally, particular examples of growth promoters (A) are quinoline derivatives of the general formula IVa or b

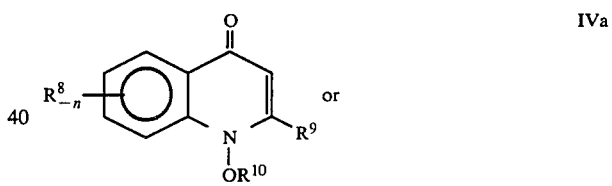

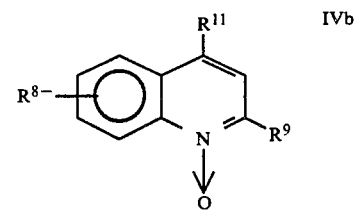

where the radicals $R^8$ are hydrogen, one or more low molecular weight alkyl or alkoxy radicals or halogen, $R^9$ is hydrogen or a low molecular weight alkyl radical and $R^{10}$ and $R^{11}$ are each hydrogen, a low molecular weight aliphatic radical or an araliphatic radical.

In a fairly general context, reductones are strongly reducing organic substances containing the structural element

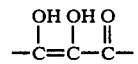

where the hydroxyl groups and the oxygen of the oxo group can furthermore be replaced with the corresponding amine functions.

Various authors have proposed the use of reductones as antioxidants for organic materials, in particular for foodstuffs.

For example, Obate et al. (Nippon Nogei Kagakv Kaishi 45 (11) (1971), 489–495; C.A. 77, 1972, Ref. No. 3944 m) investigated ascorbic acid (L-3,4-dihydroxy-5-(1,2-dihydroxyethyl)-2,5-dihydrofuran-2-one), triose reductone (2,3-dihydroxyacrolein), 2,3-dihydroxypent-2-en-1-one and a few aminoacid derivatives of the triose reductone

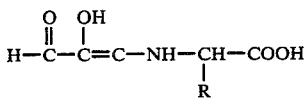

where R is H, methyl, propyl, butyl or mercaptopropyl, as well as various anils of the triose reductone (Nippon Nogei Kagaku Kaishi, 54 (7) (1980), 542–544; C.A. 93, 1980, Ref. No. 166 211 q).

In general, the two publications show that the derivatives of triose reductone are not very suitable additives for foodstuffs and feeds, especially because these very sensitive compounds are very difficult to prepare.

Furthermore, U.S. Pat. No. 3,816,137 discloses that certain 3-amino derivatives of 2,3-dihydroxycyclohex-2-en-1-one can be used as photographic developers. These amino derivatives are derived from methylamine, dimethylamine and principally from the heterocyclic amines piperidine and morpholine. These reductones are prepared by reacting the particular amine with 3-chlorocyclohexane-1,2-dione in the presence of triethylamine. However, this process, which is described in detail by H. Simon et al. (Chem. Ber. 98 (1965), 3,692–3,702), is not very suitable for industrial purposes because the 3-chlorocyclohexane-1,2-diones are not readily obtainable, and furthermore the process proceeds in more than one way when primary amines are used.

Furthermore, it is known from the paper by Cocker et al. (J. Chem. Soc. 1950, pages 2,052–2,058) than triose reductone can be reacted with aromatic amines and with $\alpha$-aminoacids to give the corresponding 3-substituted 2,3-dihydroxyacroleins. In the case of the aminoacids, however, the yields are about 10–36%, based on the triose reductone, and are hence unsatisfactory.

In comparison, the aminoreductones of the formula I are obtained by the procedure described in German Patent Application No. P 31 51 534.7 in a remarkably smooth reaction and in high yields by reacting a 2,3-dihydroxycyclohex-2-en-1-one of the general formula V

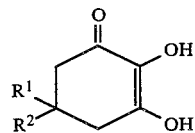 V with an amino compound of the general formula VI

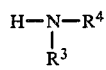 VI or with a mineral acid salt of this.

The starting compounds of the formula V, among which those in which $R^1$ and $R^2$ are each hydrogen are preferred, are known or are obtained by a conventional method, for example using the process described in Houben-Weyl, Methoden der organischen Chemie, Volume 6/1 d, page 266, by hydrogenation of pyrogallol in alkaline solution.

Particularly suitable amino compounds of the formula VI are those in which $R^3$ is hydrogen and $R^4$ is derived from a natural $\alpha$- or $\beta$-aminoacid containing one or more primary amino groups. The term natural aminoacids is used in the conventional sense to mean those aminoacids which occur in nature as building blocks, particularly of proteins, or as products of metabolic processes. These acids as well as their $C_1$–$C_{10}$-alkyl esters are physiologically tolerated and therefore result in the compounds of the formula I also being physiologically tolerated; in metabolic processes, the latter compounds can be initially decomposed to give an amino compound of the formula VI and a reductone of the formula V, or an oxidation product of this, these, on the basis of findings to date, likewise being tolerated.

The reaction products of the compounds of the formula V with the $\beta$-aminoacids are either the corresponding free acids of the formula VIIa or their lactones of the formula VIIb

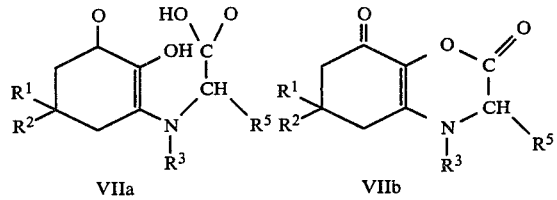

VIIa      VIIb where $R^5$ is a characteristic radical of an $\alpha$-aminoacid conforming to the definition.

A further group of particularly suitable amino compounds of the formula V comprises the $C_1$–$C_{20}$-alkylamines and alkenylamines, which can also carry hydroxyl groups, and their N-methyl and N-ethyl derivatives.

Examples of suitable compounds of this type are methylamine, dimethylamine, ethylamine, ethylmethylamine, diethylamine, propylamine, isopropylamine, butylamine, hexylamine, 2-ethylhexylamine, dodecylamine, palmitylamine and stearylamine.

These and other amines conforming to the definition can be substituted by hydroxyl groups which in turn can be etherified with a $C_1$–$C_4$-alkanol or esterified with a $C_1$–$C_4$-fatty acid. Preferably, the hydroxyl group or the alkoxy or acyloxy group is in the 2-position with respect to the amino group, since the corresponding alkanolamines, eg. ethanolamine, aminopropan-2-ol, N-methylethanolamine, aminobutan-2-ol, aminohexan-2-ol or aminododecan-2-ol, can be readily prepared by reacting the appropriate 1,2-epoxide compounds, which in turn are obtainable from the corresponding $\alpha$-olefins, with ammonia, methylamine or ethylamine.

To prepare the aminoreductones of the formula I, for example, 1 mole of a compound of the formula V is reacted with from 1 to 3 moles, preferably with an equimolar or roughly equimolar amount, of an amine of the formula VI in the absence of a solvent or in the presence of a liquid, such as toluene or xylene, which is preferably aprotic and in which the reactants need not be dissolved, at about 30°–150° C., in particular 50°–120° C. The presence of water is not troublesome in some cases; in other cases it is in any case advantageous to remove the water in the course of the reaction, together with the water formed.

If an α-aminoacid is used, either an open-chain derivative of the formula VIIa or a derivative of the formula VIIb, which has undergone cyclization to form the lactone, is obtained. If water is present, the open-chain derivative of the formula VIIa is predominantly formed, whereas if the water is removed the lactone of the formula VIIb is generally formed. Frequently, mixtures of VIIa and VIIb (which can be used in this form) are obtained, since the compounds hydrolyze in the presence of water, as is indeed the case under physiological conditions, to give the open-chain compound VIIa.

It is advisable to accelerate the reaction by using a catalytic amount of an acid, eg. hydrochloric acid or p-toluenesulfonic acid, or of an acidic ion exchanger, although the reaction also takes place in the absence of an acid.

Since both the aminoreductones of the formula I and the reductones of the formula V are sensitive to oxidation, it is obvious that the procedure should be carried out in the absence of atmospheric oxygen, for example by carrying out all operations under nitrogen.

Preferred compounds of the formula I are those in which $R^1$, $R^2$ and $R^3$ are each hydrogen or methyl. Particularly suitable radicals $R^4$ are those derived from the simple aminoacids glycine, alanine, valine, leucine, serine, thyrosine and β-alanine, as well as the $C_2$–$C_{10}$-alkylamines and their 2-hydroxy derivatives and the amines of the polyether type.

Examples of suitable growth promoters (A) are those listed in the abovementioned chapter entitled Additives in Complete Feeds in the German Feedstuffs Law. Particularly suitable components (A) of the mixture are the growth promoters from the class comprising the quinoxaline di-N-oxides, typical examples of which are the commercial products carbadox, olaquindox and cyadox.

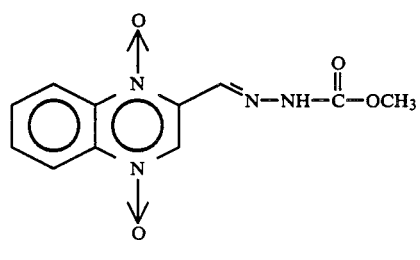

Carbadox

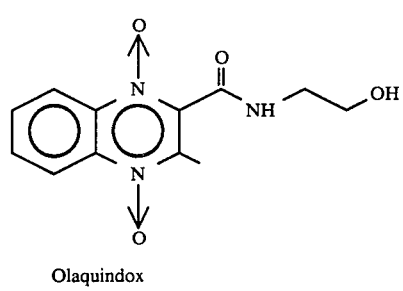

Olaquindox

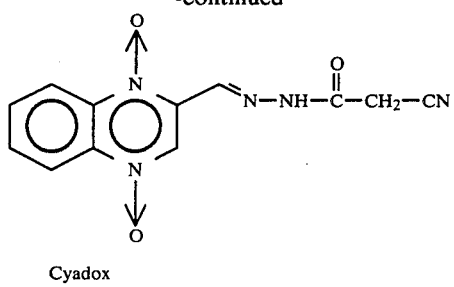

Cyadox

However, the quinoline N-oxide derivatives of the general formulae IVa and Ivb which are described in German Patent Application No. P 31 19 384.6 are particularly preferred, since these have little or no antibiotic activity and, when mixed with the aminoreductones of the formula I which are known to be non-toxic on the basis of knowledge to date, therefore give a combination which causes very little pollution.

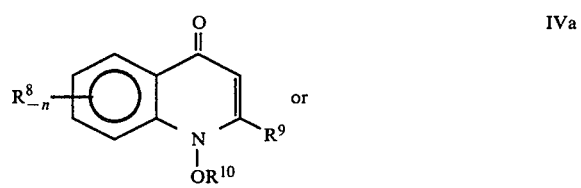

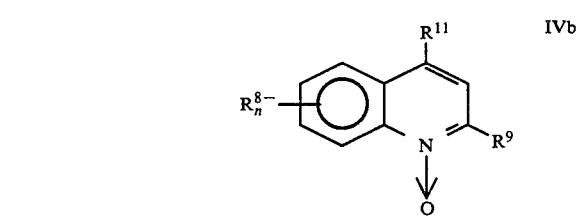

where $R^8$, $R^9$, $R^{10}$ and $R^{11}$ have the meanings stated at the outset.

Where $R^{10}$ or $R^{11}$ is H, the compounds of the formulae IVa and IVb can be present in a tautomeric equilibrium.

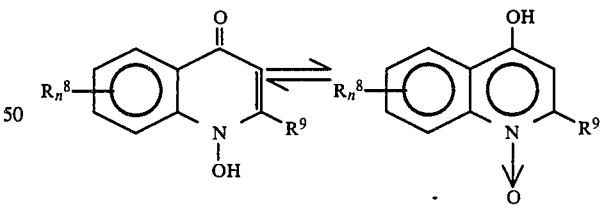

The compounds of the formulae IVa and IVb can be prepared, for example, from the appropriately substituted 4-hydroxyquinolines of the formula VIII

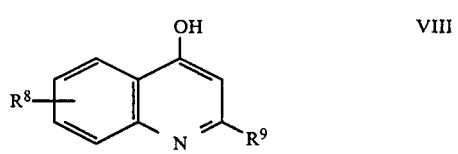

where $R^8$ and $R^9$ have the above meanings. These hydroxyquinolines are obtained in a conventional manner, for example by condensation of an appropriate aniline with a β-ketoester in accordance with equations (1) and (2), as described in German Pat. No. 455,387.

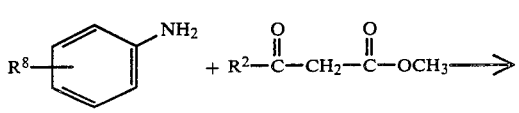
(1)

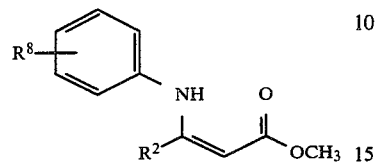
(2)

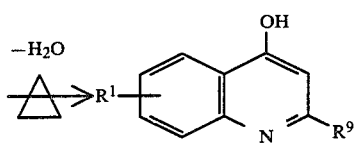

The 4-hydroxyquinolines, or the 4-alkoxy- or 4-benzyloxyquinolines obtained by alkylation, can be oxidized to the corresponding compounds of the formulae IVa and Ivb by peracids or $H_2O_2$ in a solution containing acetic acid, preferably by peracetic acid, perphthalic acid or m-chloroperbenzoic acid, in the presence or absence of molybdic or tungstic acid as a catalyst. In the case of the oxidation of the 4-hydroxyquinolines, the 4-hydroxyl group is advantageously protected by esterification with acetic acid, chlorocarbonate or benzoic acid. When the oxidation is complete, this protective group can be readily removed by stirring with dilute sodium hydroxide solution or potassium hydroxide solution at from 0° to 60° C., preferably from 10° to 30° C. Subsequent acidification precipitates the product in good purity.

The novel compounds of the formula Iva, where $R^{10}$ is not H, are obtained from the intermediate (where $R^{10}$ is H) by alkylation with a dialkyl sulfate or sulfite or the appropriate alkyl halide. The reaction media used are polar solvents, such as tetrahydrofuran, dioxane, ether or dimethylformamide, in the presence or absence of a base, as well as water.

The novel active ingredient combination consisting of an aminoreductone of the formula I and a growth promoter (A) is a particularly preferred one when the component (A) is a compound of the formula II, III or IV.

The concentration required to achieve the best effect is from 0.1 to 100, particularly preferably from 0.1 to 25, ppm for each component, the ratio of the active ingredients (A) to (B) being from 50:1 to 1:50, preferably from 10:1 to 1:10. The optimum ratio varies depending on the animal species, and is, for example, 1:1 in the case of rats, if, for example, a mixture of the compounds of the formulae

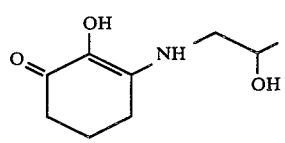

aminoreductone

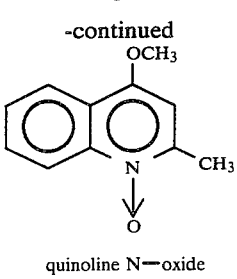

quinoline N—oxide is used.

The active ingredient combination can be administered to the animals in the conventional feed, as well as with the drinking water. Such mixtures can be prepared using, for example, premixes (or feed additives) containing from 1 to 50% of active ingredient combination. Although it is of course possible to process the synergistic components separately to give premixes and only then to combine these to give the finished feed, it appears particularly advantageous to mix the active ingredient combination with the premix or the concentrate in the correct ratio and then to establish the final concentration by diluting the concentrate with the commercial feed, since this ensures the correct concentration and the correct mixing ratio in the final feed. The feed premixes, feed concentrates and feeds can contain, as the carrier, any substance of vegetable or animal origin which is used for feeding. Advantageous carriers are wheat middlings, barley, rye, oatmeal, rice bran, wheat bran, soybean meal, ground corn germ, bonemeal, ground lucerne, soybean middlings, animal meal and fishmeal, as well as mixtures of these.

The feed premixes, feed concentrates and feeds advantageously contain, as assistants, silicon dioxide, wetting agents, antioxidants, starch, dicalcium phosphate, monocalcium phosphate, calcium carbonate and/or sorbic acid. The wetting agents can be, for example, non-toxic oils, advantageously soybean oil, corn oil or paraffin oil. The various alkylene glycols have also proven advantageous wetting agents. The starch is advantageously corn starch, wheat starch or potato starch. If desired, the compounds of the formula I, II, III and IV may also be applied on carrier materials and microencapsulated or coated with gelatin, either individually or in combination.

By mixing the appropriate amounts of the concentrates according to the invention into the specific feed mixture for each animal species, it is possible in each case to obtain the optimum active ingredient combination and the amount of active ingredient for each animal species.

EXAMPLES

Preparation of the Aminoreductones

The radical

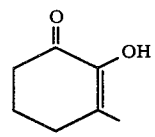

is referred to below as radical A. All syntheses of aminoreductones are carried out under nitrogen.

EXAMPLE 1

A—NH—CH₂—COOH 106.5 g (0.83 mole) of A—OH and 75 ml of 2N hydrochloric acid were added to a solution of 150 g (2 moles) of glycine and 450 ml of water, while stirring, and the mixture was heated to the boil. At about 40° C., a clear solution was formed, from which the product began to be precipitated at about 80° C. When the boiling point was reached, the mixture was cooled to 10° C., and the precipitate, a yellowish crystalline powder, was worked up in a conventional manner. Recrystallization from hot isopropanol gave the above aminoreductone in 88% yield, in the form of colorless crystals of melting point 185°–187° C.

EXAMPLE 2

A—NH—CH₂—COO—C₂H₅

A mixture of 128 g (1 mole) of A—OH, 149.5 g (1 mole) of glycine ethyl ester hydrochloride, 84 g (1 mole) of NaHCO₃ and 1 liter of toluene was heated at the boil for about 2 hours, the water of reaction being separated off continuously. After the reaction mixture had been cooled to 25° C., the NaCl formed was separated off, and washed with 1 liter of ethanol. The toluene and ethanol phases were combined and then evaporated down under reduced pressure at 40° C., and the residue was recrystallized from 0.2 liter of ethanol with the addition of active carbon to give colorless crystals of melting point 121°–123° C. Yield: 60%.

EXAMPLE 3

A—NH—n—C₁₂H₂₅

A mixture of 145 g (0.78 mole) of dodecylamine, 100 g (0.78 mole) of A—OH, 1 g of p-toluenesulfonic acid and 50 ml of toluene was heated at the boil for about 1 hour, the water of reaction being separated off, after which 500 ml of n-hexane were added at 60° C. On further cooling, the product separated out as a yellowish crystal slurry. The product was recrystallized from n-hexane to give a pure compound of melting point 79°–81° C., and a yield of 81%. The compound was obtained in the form of colorless lamellae.

EXAMPLES 4 TO 15

A—NR³—R⁴

Various amino compounds HNR³—R⁴ were reacted with A—OH by a method similar to that described in Example 3. The results are shown in Table 1.

TABLE 1

| Example | Compound A—NR³—R⁴ | mp. °C. | Yield % |
|---|---|---|---|
| 4 | A—NH—CH₂CH₂—OH | 164–165 | 63 |
| 5 | A—NH—CH(CH₃)—COOH | 227–229 | 51 |
| 6 | A—NH—CH₂—CH₂—COOH | 121–123 | 80 |
| 7 | A—NH—CH₂—CH₂—COO—CH₃ | 96–98 | 60 |
| 8 | A—NH—CH₃ | 175–178 | 48 |
| 9 | A—NH—CH₂—CH(CH₃)—OH | 106–107 | 57 |
| 10 | A—N(CH₃)—CH₂—CH₂—OH | liquid | 64 |
| 11 | A—NH—n-hexyl | 101–102 | 70 |
| 12 | A—NH—n-tridecyl | 86–87 | 70 |
| 13 | A—NH—2-ethylhexyl | liquid | 90 |
| 14 | A—N(CH₃)—2-ethylhexyl | liquid | 70 |
| 15 | A—NH—(CH₂—CH₂—O)₂H | 85–89 | 52 |

EXAMPLE 16

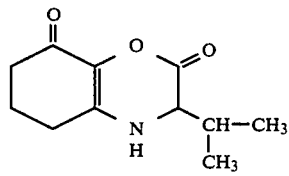

A mixture of 12.8 g (0.1 mole) of A—OH, 12.9 g (0.11 mole) of D,L-valine, 50 ml of toluene and 1 g of p-toluenesulfonic acid was heated at the boil for about 2 hours, the water of reaction being separated off. During this time, 3.6 ml (0.2 mole) of water were removed.

The reaction mixture was then cooled, the product crystallizing out. The crystalline mass was isolated, and recrystallized from ethanol. The yield of the pure lactone was 57%, the product being obtained in the form of colorless crystals of melting point 170°–171° C.

Preparation of Growth Promoters

EXAMPLE 17

86.5 g (0.5 mole) of 4-methoxyquinaldine (prepared from 4-hydroxyquinaldine in accordance with M. Marin, A. Ch. 4 [11] (1935), 301, 335) were dissolved in 250 ml of ethyl acetate at room temperature, and 105 g (0.55 mole) of 90% strength 3-chloroperbenzoic acid were added a little at a time, while stirring. The mixture was heated at 40° C. for 4 hours, after which stirring was continued overnight at room temperature, the product being precipitated. The mixture was cooled in an icebath, the product was filtered off under suction and washed with a little cold ethyl acetate, the filter cake was then dissolved in an amount of methanol just sufficient for this purpose, and the solution was filtered over a basic ion exchanger (eg. 1 liter of Lewatit MP 600). Evaporating down under reduced pressure in a rotary evaporator gave 45.1 g of slightly yellowish crystals of melting point 130°–131° C.

EXAMPLE 18

108.5 g (0.5 mole) of 6-ethoxy-4-methoxyquinaldine (prepared from 6-ethoxy-4-hydroxyquinaldine in accordance with M. Marin, A. Ch. 3 [11] (1935), 301, 335) were reacted with m-chloroperbenzoic acid in ethyl acetate by the method described in Example 17. Filtering over Lewatit MP 600 and evaporating down under reduced pressure in a rotary evaporator gave 79 g of colorless crystals of melting point 134°–136° C.

EXAMPLE 19

80 g (0.5 mole) of 4-hydroxyquinaldine were converted with 27 g (0.5 mole) of NaOCH$_3$ in 400 ml of dry methanol to the Na salt. The methanol was removed by evaporation under reduced pressure from a waterpump, after which the dry Na salt was suspended in 700 ml of dry toluene, and 54 g (0.5 mole) of ethyl chloroformate were added slowly at 80° C. After 2 hours, the solvent was distilled off under reduced pressure from a waterpump, and the residue was stirred for 30 minutes in 600 ml of methylene chloride and then filtered off under suction.

82.5 g (0.5 mole) of 85% strength m-chloroperbenzoic acid were added a little at a time to the filtrate at 15° C. After one hour, the mixture was extracted by shaking with cold dilute sodium carbonate solution and with water, the organic phase was dried and evaporated down under reduced pressure from a waterpump, the residue was taken up in 200 ml of 50% strength ethanol, and a solution of 16 g of KOH in 200 ml of 50% strength ethanol was added at room temperature. After 30 minutes, the solution was evaporated down to half its volume, and the product was precipitated by acidifying the solution to pH 4 with 2N HCl. 47–60 g of crude product were obtained. If desired, this can be recrystallized from methanol to give pure 4-hydroxyquinaldine N-oxide. Mp.: 248°–250° C.

EXAMPLE 20

14 g (0.08 mole) of 4-hydroxyquinaldine N-oxide were suspended in 400 ml of dioxane, and 4.8 g (0.12 mole) of NaOH in 80 ml of H$_2$O were added. The mixture was stirred at 50° C., and 13.2 g (0.116 mole) of dimethyl sulfate in 80 ml of dioxane were added dropwise. After 2 hours, the solution was evaporated down under reduced pressure from a waterpump, the residue was taken up in 20 ml of water, the solution was acidified to pH 1 with concentrated HCl, and the product was filtered off under suction and dried. 14 g of crude product were obtained. This can be recrystallized from water with the addition of active carbon. Yield: 6–8 g of N-methoxyquinald-4-one; mp.: 186°–188° C./decomposition.

EXAMPLES 21 TO 28

The compounds below were obtained by methods similar to those described in Examples 17 to 20:

| | | Mp. [°C.] | Analysis | | | | | | |
|---|---|---|---|---|---|---|---|---|---|
| 21 | 6-EtO-N-OH-2-methyl-quinolin-4-one | 248–250 | C | 65.74 | H | 5.98 | N | 6.39 | calculated |
| | | | | 65.7 | | 6.0 | | 6.4 | found |
| 22 | 8-CH$_3$-N-OH-2-methyl-quinolin-4-one | 253–254 | C | 69.83 | H | 5.86 | N | 7.40 | calculated |
| | | | | 70.0 | | 6.1 | | 7.7 | found |
| 23 | N-OCH$_3$-2-methyl-quinolin-4-one | 186–188 (decomposition) | C | 69.84 | H | 5.86 | N | 7.40 | calculated |
| | | | | 70.1 | | 6.0 | | 7.5 | found |
| 24 | 6-CH$_3$-N-OH-2-methyl-quinolin-4-one | 248–252 | C | 69.83 | H | 5.86 | N | 7.40 | calculated |
| | | | | 70.3 | | 5.9 | | 7.6 | found |
| 25 | 6-Cl-N-OH-2-methyl-quinolin-4-one | 265–267 (decomposition) | C | 57.28 | H | 3.82 | N | 6.68 | calculated |
| | | | | 57.1 | | 3.8 | | 6.7 | found |

| | | Mp. [°C.] | Analysis | | | | | | |
|---|---|---|---|---|---|---|---|---|---|
| 26 | (structure: 6-chloro-N-methoxy-2-methyl-quinolin-4(1H)-one) | 128–133 | C | 59.06 | H | 4.47 | N | 6.26 | calculated |
| | | | | 59.3 | | 4.7 | | 6.3 | found |
| 27 | (structure: 6-butyl-4-methoxy-2-methylquinoline N-oxide) | ¼ H₂O 65–68° C. | C | 72.1 | H | 7.81 | N | 5.61 | calculated |
| | | | | 71.8 | | 8.0 | | 5.6 | found |
| 28 | (structure: 6-ethoxy-4-methoxy-2-pentylquinoline N-oxide) | 106 | C | 68.4 | H | 8.55 | N | 5.2 | calculated |
| | | | | 68.3 | H | 8.7 | N | 5.1 | found |

Use Examples

EXAMPLE 29

For piglets, a premix having the following composition was prepared:

| Constituents | Amount |
|---|---|
| Vitamin A | 1,200,000 IU |
| Vitamin $D_3$ | 300,000 IU |
| Vitamin E | 2,000 IU |
| Vitamin $B_2$ | 600 mg |
| Vitamin $B_3$ | 2,000 mg |
| Vitamin $B_{12}$ | 5 mg |
| Nicotinic acid (niacin) | 3,000 mg |
| Choline chloride | 40,000 mg |
| 4-Methoxyquinaldine N—oxide (from Example 17) | 1,000 mg |
| 3-Isopropanolamino-2-hydroxycyclohexane (from Example 9) | 1,000 mg |
| Butylhydroxytoluene (antioxidant) | 30,000 mg |
| Trace elements | |
| Manganese | 6,000 mg |
| Iron | 10,000 mg |
| Zinc | 15,000 mg |
| Copper | 30,000 mg |
| Iodine | 100 mg |
| doubly ground bran to make up to | 1,000 g |

This vitamin and trace element premix was added to the basic feed in an amount of 0.5 kg per 100 kg.

EXAMPLE 30

0.5 kg of the premix prepared as described in Example 29 was mixed with a basic feed having the following composition:

| Component | Amount |
|---|---|
| Corn | 25.0 kg |
| Wheat | 34.0 kg |
| Soybean extract | 18.0 kg |
| Milk powder | 9.9 kg |
| Fishmeal | 4.0 kg |
| Feed yeast | 2.0 kg |
| Fat powder | 3.4 kg |
| Mineral premix (55:40:5 dicalcium phosphate/monocalcium phosphate/calcium carbonate mixture) | 1.8 kg |
| Feed lime | 1.0 kg |
| Feed-quality sodium chloride | 0.4 kg |
| Premix from Example 29 | 0.5 kg |
| Total weight | 100.0 kg |

The resulting piglet feed contained 5 ppm (0.0005% by weight) of each synergistic component (from Examples 9 and 17).

EXAMPLE 31

The activity of the novel feeds with regard to growth promotion may be illustrated by means of a feeding experiment on rats:

The test animals, male SPF Wistar rats (from Hagemann, Extertal), were kept in groups of three in Makrolon cages and fed with commercial experimental feed (Eggersmann, Rinteln). Feed and water were available in unrestricted amounts. The results are shown in Table 2.

EXAMPLE 32

A feeding experiment on pigs demonstrated the increased activity of the novel mixture compared with commercial active ingredients (Table 3).

TABLE 2

Feeding experiments on rats (SPF Wistar)

| Active ingredient combination | | Concentration in the feed | | Number of animals | Live weight in g | | Change compared with control |
|---|---|---|---|---|---|---|---|
| A (x) | B (x) | A | B | n | 0 day | 21 days | (= 100%) |
| Control | — | — | — | 250 | 62.7 ± 1.5 | 178.0 ± 3.0 | ±0 |
| Carbadox | — | 50 ppm | — | 20 | 62 ± 2.3 | 184.1 ± 6.0 | +5.5% |
| Carbadox | — | 25 ppm | — | 40 | 62.5 ± 2.3 | 177.7 ± 2.4 | +0.1% |
| Carbadox | 9 | 50 ppm | 20 ppm | 9 | 63.2 ± 2.9 | 184.6 ± 8.9 | +5.3% |
| Carbadox | 9 | 25 ppm | 20 ppm | 10 | 62.9 ± 2.2 | 186.4 ± 9.2 | +7.1% |
| Carbadox | 9 | 10 ppm | 10 ppm | 10 | 62.6 ± 3.4 | 187.4 ± 8 | +8.2% |
| 21 | — | 50 ppm | — | 10 | 63.3 ± 3.6 | 178.4 ± 11.3 | ±0% |
| 21 | 9 | 50 ppm | 10 ppm | 10 | 62.1 ± 2.5 | 182.2 ± 9.9 | +4.2% |
| 17 | — | 25 ppm | — | 10 | 65.0 ± 5 | 180.9 ± 6.2 | +0.5 |
| 17 | — | 10 ppm | — | 10 | 62.9 ± 2.1 | 180.6 ± 8.8 | +2.1% |
| 17 | 126 | 10 ppm | 10 ppm | 20 | 62.6 ± 2.2 | 187.2 ± 13 | +8.1% |
| 18 | 126 | 50 ppm | 20 ppm | 10 | 63.2 ± 3.8 | 185.0 ± 11 | +5.6% |
| 18 | 126 | 5 ppm | 10 ppm | 10 | 64.3 ± 4.3 | 191.2 ± 12 | +10% |
| 17 | 6 | 10 ppm | 10 ppm | 10 | 62.7 ± 2.3 | 186.3 ± 11 | +7.2% |
| 17 | 3 | 10 ppm | 10 ppm | 10 | 62.1 ± 3.8 | 185.4 ± 9 | +6.9% |

(x)No. of the Synthesis Example

TABLE 3

| Active ingredient combination | | Concentration in the feed | | Number of animals | Live weight initially kg | after 58 days kg | Change compared with control |
|---|---|---|---|---|---|---|---|
| A (x) | B (x) | A | B | | | | |
| Control | — | — | — | 5 ♂ 5 ♀ | 14.5 ± 0.7 | 42.9 ± 5.8 | ±0% |
| Carbadox | — | 25 ppm | — | 5 ♂ 5 ♀ | 14.4 ± 0.9 | 45.7 ± 7.4 | +10.2% |
| 17 | — | 6 ppm | — | 4 ♂ 4 ♀ | 14.4 ± 0.6 | 42.3 ± 6.3 | −1.7% |
| 17 | 9 | 6 ppm | 12 ppm | 5 ♂ 5 ♀ | 14.5 ± 1.1 | 46.2 ± 5.5 | +11.6% |
| Control | — | — | — | 5 ♂ 5 ♀ | 12.5 ± 1.3 | 41.9 ± 5.8 | ±0% |
| 18 | — | 6 ppm | — | 5 ♂ 5 ♀ | 12.1 ± 2.0 | 43.5 ± 10.5 | +6.8% |
| 18 | 9 | 6 ppm | 8 ppm | 5 ♂ 5 ♀ | 12.1 ± 0.2 | 45.3 ± 5.5 | +12.9% |
| Carbadox | — | 25 ppm | — | 5 ♂ 5 ♀ | 13.7 ± 1.0 | 45.0 ± 7.7 | +6.4% |
| Carbadox | 9 | 10 ppm | 8 ppm | 5 ♂ 5 ♀ | 13.9 ± 0.9 | 45.4 ± 6.5 | +7.2% |
| Control | — | — | — | 9 ♂ | 13.5 ± 1.3 | 64.5 ± 8.0 | ±0% |
| Carbadox | — | 25 ppm | — | 4 ♂ | 14.4 ± 0.9 | 73.8 ± 11.3 | +14.4% |
| 17 | 9 | 6 ppm | 12 ppm | 5 ♂ | 14.5 ± 1.0 | 83.7 ± 7.5 | +29.7% |
| 17 | 9 | 6 ppm | 8 ppm | 5 ♂ | 12.1 ± 0.3 | 81.0 ± 9.0 | +25.6% |

(x)No. of the Synthesis Example

We claim:

1. A mixture which contains
(A) a commercial growth promoter selected from the group consisting of compounds of the formulae II, III and IVa and b

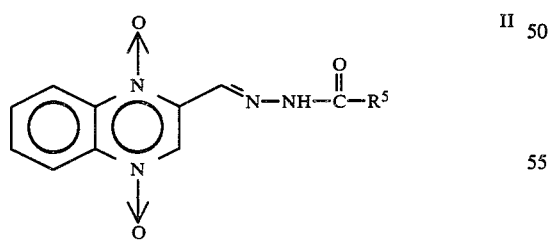

II

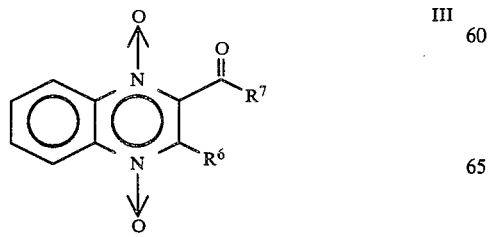

III

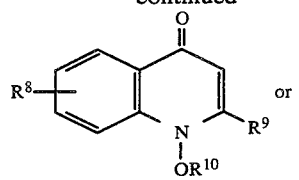

IV a

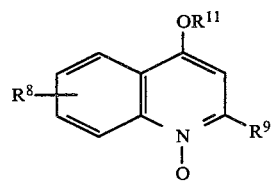

IV b where $R^5$ is $C_1$-$C_6$-alkyl which can be substituted by halogen or cyano, or is $C_1$-$C_6$-alkoxy, $R^6$ is hydrogen or a low molecular weight alkyl radical, $R^7$ is a low molecular weight alkyl, alkoxy or alkylamine radical, these radicals being unsubstituted or substituted by hydroxyl or alkoxy groups, $R^8$ is hydrogen, one or more low molecular weight alkyl or alkoxy radicals or halogen, $R^9$ is hydrogen or a low molecular weight alkyl radical and $R^{10}$ and $R^{11}$ are each hydrogen, a low molecular weight aliphatic radical or an araliphatic radical,
(B) an aminoreductone of the formula I

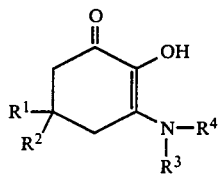

where $R^1$, $R^2$ and $R^3$ are identical or different and are each hydrogen, methyl or ethyl and $R^4$ is a straight-chain or branched $C_1$–$C_{20}$-alkyl or alkenyl group which can carry one or more hydroxyl groups, low molecular weight alkoxy groups or low molecular weight acyloxy groups, or is a radical —$(CH_2—CH_2—O)_n$, where n is from 1 to 10, which can be etherified with a low molecular weight alkanol or esterified with a low molecular weight carboxylic acid, or is the radical, bonded at the amino group, of a natural α- or β-aminoacid or a $C_1$–$C_{10}$-alkyl ester of this, or, in the case of an α-aminoacid, is a radical in which the carboxyl group of the aminoacid and the 2-hydroxyl group of the cyclohexenone ring form a lactone, or its physiologically tolerated salt with a mineral acid, the weight ratio of the growth promoter (A) to the aminoreductone (B) being from 50:1 to 1:50.

2. A mixture according to claim 1 which consists of (A) one or more of the compounds 4-hydroxyquinaldine N-oxide, 6-methyl-4-hydroxyquinaldine N-oxide, 6-ethoxy-4-hydroxyquinaldine N-oxide, 6-ethoxy-4-methoxyquinaldine N-oxide, 6-chloro-4-hydroxyquinaldine N-oxide, 8-methyl-4-hydroxyquinaldine N-oxide, 6-butyl-4-methoxyquinaldine N-oxide, 6-ethoxy-4-methoxy-2-pentylquinoline N-oxide and (B) one or more of the compounds 3-ethanolamino-2-hydroxycyclohexenone, 3-isopropanolamino-2-hydroxycyclohexenone, 3-β-alanino-2-hydroxycyclohexenone, 3-glycino-2-hydroxycyclohexenone, 3-dodecyclamino-2-hydroxycyclohexenone and 3-(-hydroxydodecylamino)-2-hydroxycyclohexenone.

3. The mixture of claim 1, in the form of a dry powder, wherein the components (A) and (B) are present in coated or microencapsulated form and the weight ratio of components (A) to (B) is from 10:1 to 1:10.

4. A growth-promoting feed or drinking liquid which contains, in addition to a conventional feed premix, feed concentrate or feed, or water, which is present as the principal component, a small amount of a mixture as defined in claim 1.

5. A feed or drinking liquid as defined in claim 4, which contains from 0.1 to 500 ppm of the mixture.

6. A feed or drinking liquid as defined in claim 4, which contains from 0.1 to 500 ppm of a compound of the formula I and from 0.1 to 500 ppm of a compound of the formula II.

7. A feed or drinking liquid as defined in claim 4, which contains from 0.1 to 500 ppm of a compound of the formula I and from 0.1 to 500 ppm of a compound of the formula III.

8. A feed or drinking liquid as defined in claim 4, which contains from 0.1 to 500 ppm of a compound of the formula I and from 0.1 to 500 ppm of a compound of the formula IVa or b.

* * * * *

UNITED STATES PATENT AND TRADEMARK OFFICE
CERTIFICATE OF CORRECTION

PATENT NO. : 4,616,016
DATED : October 7, 1986
INVENTOR(S) : Peter LECHTKEN et al.

It is certified that error appears in the above-identified patent and that said Letters Patent is hereby corrected as shown below:

IN THE CLAIMS:

Claim 1, column 17, line 16, change "$-(CH_2-CH_2-O)_n$" to -- $-(CH_2-CH_2-O)_nH$ --

Signed and Sealed this

Thirteenth Day of January, 1987

Attest:

DONALD J. QUIGG

Attesting Officer

Commissioner of Patents and Trademarks